US012653598B2

(12) United States Patent
Zhang et al.

(10) Patent No.: US 12,653,598 B2
(45) Date of Patent: Jun. 16, 2026

(54) APPARATUSES AND METHODS FOR ASYMMETRIC ICE FORMATION DURING CRYOABLATION TREATMENTS

(71) Applicant: Varian Medical Systems, Inc., Palo Alto, CA (US)

(72) Inventors: Hongxuan Zhang, Austin, TX (US); Ryan Lee Medema, Georgetown, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 816 days.

(21) Appl. No.: 17/664,231

(22) Filed: May 20, 2022

(65) Prior Publication Data

US 2023/0371997 A1     Nov. 23, 2023

(51) Int. Cl.
*A61B 18/02* (2006.01)
*G16H 40/67* (2018.01)
*A61B 18/00* (2006.01)

(52) U.S. Cl.
CPC ............. *A61B 18/02* (2013.01); *G16H 40/67* (2018.01); *A61B 2018/00041* (2013.01); *A61B 2018/00577* (2013.01); *A61B 2018/00642* (2013.01); *A61B 2018/00982* (2013.01); *A61B 2018/0262* (2013.01)

(58) Field of Classification Search
CPC ................... A61B 18/02; A61B 18/08; A61B 2018/00577; A61B 2018/00642; A61B 2018/0262
See application file for complete search history.

(56) References Cited

U.S. PATENT DOCUMENTS

| | | | |
|---|---|---|---|
| 3,910,277 A | 10/1975 | Zimmer | |
| 5,906,612 A * | 5/1999 | Chinn | A61B 18/02 |
| | | | 606/23 |
| 6,575,969 B1 * | 6/2003 | Rittman, III | A61B 18/1482 |
| | | | 606/41 |
| 9,622,806 B2 | 4/2017 | Mihalik | |
| 2002/0128638 A1 * | 9/2002 | Chauvet | A61B 18/02 |
| | | | 607/113 |
| 2006/0079867 A1 | 4/2006 | Berzak et al. | |

(Continued)

FOREIGN PATENT DOCUMENTS

| | | |
|---|---|---|
| EP | 3920784 A1 | 12/2021 |
| WO | 2012149341 A1 | 11/2012 |

(Continued)

OTHER PUBLICATIONS

International Search Report and Written Opinion for PCT/US2023/022689 issued Sep. 20, 2023.

*Primary Examiner* — Daniel W Fowler
(74) *Attorney, Agent, or Firm* — Morgan, Lewis & Bockius LLP; Manita Rawat

(57)        ABSTRACT

A method of performing a cryoablation treatment includes initiating a flow of cryogen to a tip of the cryoprobe and obtaining ice formation data characterizing a shape of ice forming at a target tissue in a patient. The method also includes comparing the ice formation data to a predetermined ice formation profile and energizing a heating portion on the cryoprobe to limit growth of ice in a first direction relative to a predetermined location on the cryoprobe while the cryogen flows to the tip of the cryoprobe.

10 Claims, 9 Drawing Sheets

100

(56) References Cited

U.S. PATENT DOCUMENTS

2008/0051774 A1 * 2/2008 Ofir ........................ A61B 18/02
606/20
2009/0264876 A1 * 10/2009 Roy ....................... A61B 18/02
606/20
2014/0316398 A1 * 10/2014 Kelly .................... A61B 18/02
606/24

FOREIGN PATENT DOCUMENTS

WO          2020163854  A1      8/2020
WO          2023225168  A1      11/2023

* cited by examiner

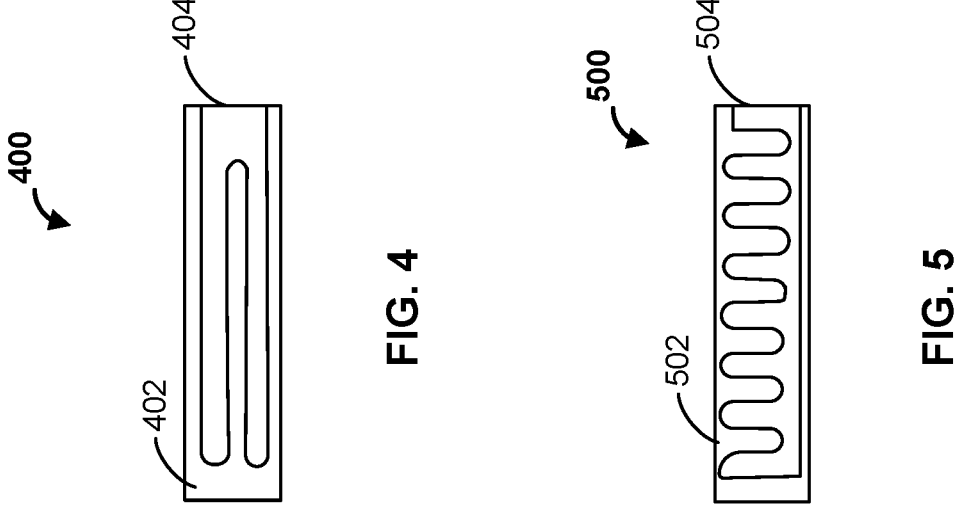
FIG. 4
FIG. 5
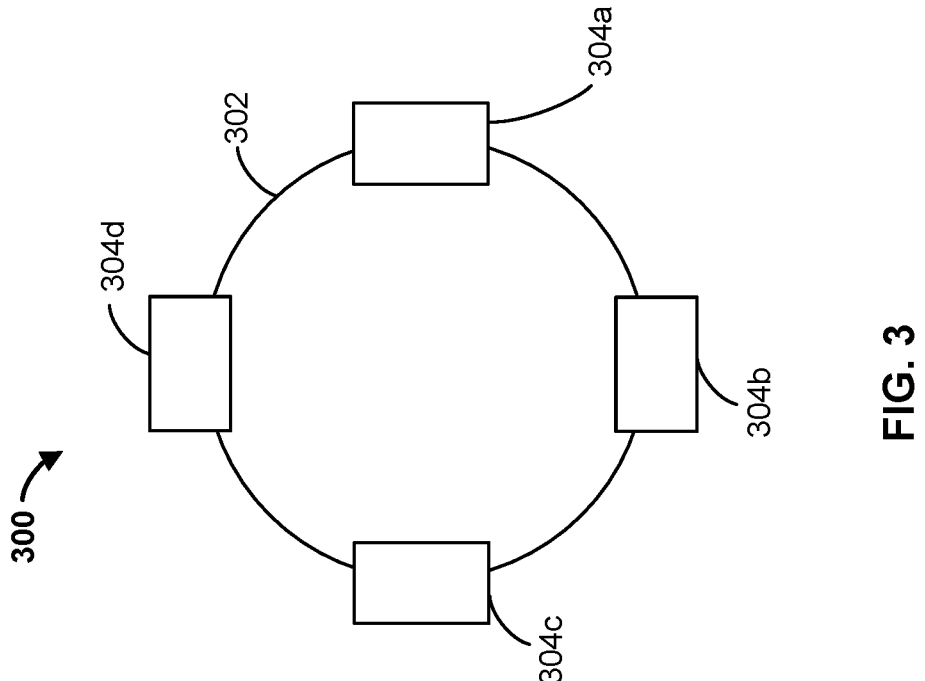
FIG. 3

APPARATUSES AND METHODS FOR ASYMMETRIC ICE FORMATION DURING CRYOABLATION TREATMENTS

FIELD

The present disclosure relates to apparatuses and methods for asymmetric formation of ice during cryoablation treatments.

BACKGROUND

This section provides background information related to the present disclosure which is not necessarily prior art.

Systems and methods for providing cryoablation treatments may include cryoablation probes that are introduced at or near target tissue in a patient. A cryoablation system may include an extremely cold cryogen (liquid, gas, or mixed phase) that may be passed through a probe in thermal contact with the target tissue. Heat from the tissue passes from the tissue, through the probe, and into the cryogen that removes heat from the targeted tissue. This removal of heat causes tissue to freeze, resulting in the destruction of the targeted tissue. When the tissue freezes, ice forms typically in an iceball. The iceball may be in the form of a sphere, ellipsoid or other shape. In existing systems, the iceball is typically formed in a symmetrical shape. It is desirable to perform cryoablation treatments such that the target tissue is completely frozen and that the freezing of surrounding tissues and/or body structures is minimized.

Traditional or existing cryoablation apparatuses, cryoprobes and methods suffer from various disadvantages. Traditional or existing systems and methods do not allow for the formation of ice in shapes that are asymmetrical relative to the cryoprobe. As such, the ice that forms using existing and traditional methods and systems may not perform as efficiently and effectively as desired. Furthermore, treatments using existing and traditional methods may unnecessarily form ice that freezes healthy tissue or body structures adjacent to or surrounding the target tissue. In addition, traditional and existing systems and methods may not destroy all of the target tissue due to a shape that does not correspond to the shape of the ice this formed during treatment. There exists a need, therefore, for improved cryoablation systems and methods to perform more efficiently and effectively with less detrimental effects on healthy tissue.

SUMMARY

This section provides a general summary of the disclosure, and is not a comprehensive disclosure of its full scope or all of its features.

In some embodiments of the present disclosure apparatuses and methods are provided that can form asymmetrical ice shapes during cryoablation treatments. The ice formation may be formed in an asymmetrical shape to correspond to a shape of a target tissue (e.g., a tumor). The ice formation may be formed in an asymmetrical shape to prevent or reduce the likelihood that healthy tissue will be harmed.

The apparatuses and methods of the present disclosure provide improved cryoprobes in some embodiments. Such cryoprobes may include various quantities of heating portions that can be independently controlled and/or energized during operation of the cryoprobe. The heating probes can reduce the formation of ice in one or more localized regions relative to the cryoprobe to cause the ice to form in a desired shape. The heating portions may be positioned in various configurations to allow the control and growth of ice in a predetermined manner as may be desired for a cryoablation treatment.

The apparatuses and methods of the present disclosure are improvements over existing and traditional apparatuses and methods. The apparatuses and methods of the present disclosure can more effectively destroy or otherwise treat the targeted tissue by forming ice that corresponds to the shape of the target tissue. In addition, the ice can be formed to reduce the amount of healthy tissue that is subjected to the low temperatures of the ice. In this manner, the detrimental effects of cryoablation treatments on healthy tissue can be reduced and/or minimized.

In some embodiments of the present disclosure, a cryoablation system may include a plurality of heating portions in which each heating portion of the plurality of heating portions is individually controllable to operate in an energized state and a de-energized state.

In one aspect, each heating portion of the plurality of heating portions may include a resistive heating element.

In another aspect, each heating portion of the plurality of heating portions may be coupled to a heater controller that is configured to change one or more heating portions of the plurality of heating portions from the de-energized state to the energized state to change an ice growth characteristic of ice forming during a freezing cycle of a cryoablation treatment.

In another aspect, each heating portion of the plurality of heating portions may be located at a different circumferential position around a center axis of the cryoablation probe.

In another aspect, each heating portion of the plurality of heating portions may be separated from adjacent heating portions.

In another aspect, the plurality of heating portions may include a first array of heating portions positioned at a first longitudinal position from a tip of the cryoablation probe and a second array of heating portions located at a second longitudinal position from the tip of the cryoablation probe.

In another aspect, the plurality of heating portions may be located in an outer shell of the probe.

In another aspect, the cryoablation probe may include a cryogen supply and a shell positioned radially outward of the cryogen supply, wherein the plurality of heating portions are configured to operate in the energized state and the de-energized state while cryogen flows from the cryogen supply.

In some embodiments, a cryoablation apparatus is provided that may include a cryoablation probe described above and at least one computing device coupled to the plurality of heating portions. The at least one computing device may be configured to compare ice formation data to a predetermined ice formation profile and energize a heating portion of the plurality of heating portions to limit growth of ice in a first direction relative to a predetermined location on the cryoablation probe while cryogen flows to a tip of the cryoprobe.

In one aspect, the at least one computing device may be further configured to modify at least one operating parameter of the cryoablation apparatus. The at least one operating parameter of the cryoablation apparatus may include one of a pressure, flow rate and temperature of a cryogen.

In some embodiments of the present disclosure, a method of performing a cryoablation treatment may include initiating a flow of cryogen to a tip of the cryoprobe and obtaining ice formation data characterizing a shape of ice forming at a target tissue in a patient. The method may also include comparing the ice formation data to a predetermined ice formation profile and energizing a heating portion on the cryoprobe to limit growth of ice in a first direction relative to a predetermined location on the cryoprobe while the cryogen flows to the tip of the cryoprobe.

In one aspect, the heating portion is a first heating portion and the method further may also include energizing a second heating portion separated from the first heating portion to limit growth of ice in a second direction relative to the predetermined location on the cryoprobe while the cryogen flows to the tip of the cryoprobe.

In another aspect, the heating portion is a first heating portion of a plurality of heating portions and each heating portion of the plurality of heating portions are positioned circumferentially around the probe at a predetermined distance from the tip of the cryoprobe.

In another aspect, the step of energizing the heating portion causes an asymmetrical ice formation to grow at the target tissue.

In another aspect, the step of energizing the heating portion may be performed when the ice formation data indicates that ice forming at the target tissue is greater than an ice formation target of the ice formation profile.

In another aspect, the ice formation data may be obtained from an imaging apparatus.

In another aspect, the method may also include de-energizing the heating portion when the ice formation data indicates that ice forming at the target tissue is less than an ice formation target of the ice formation profile.

In another aspect, the step of energizing the heating portion may include applying power according to predetermined duty cycle.

In another aspect, the predetermined duty cycle may include a pulse width modulated (PWM) duty cycle.

In another aspect, the step of energizing the heating portion causes heat to be generated asymmetrically at a desired position on the cryoprobe.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a cross-sectional view of an example cryoprobe of the present disclosure.

FIG. 4 is an illustration of an example heating portion of the present disclosure.

FIG. 5 is an illustration of another example heating portion of the present disclosure.

Corresponding reference numerals indicate corresponding parts throughout the several views of the drawings.

DETAILED DESCRIPTION

Figure 1:
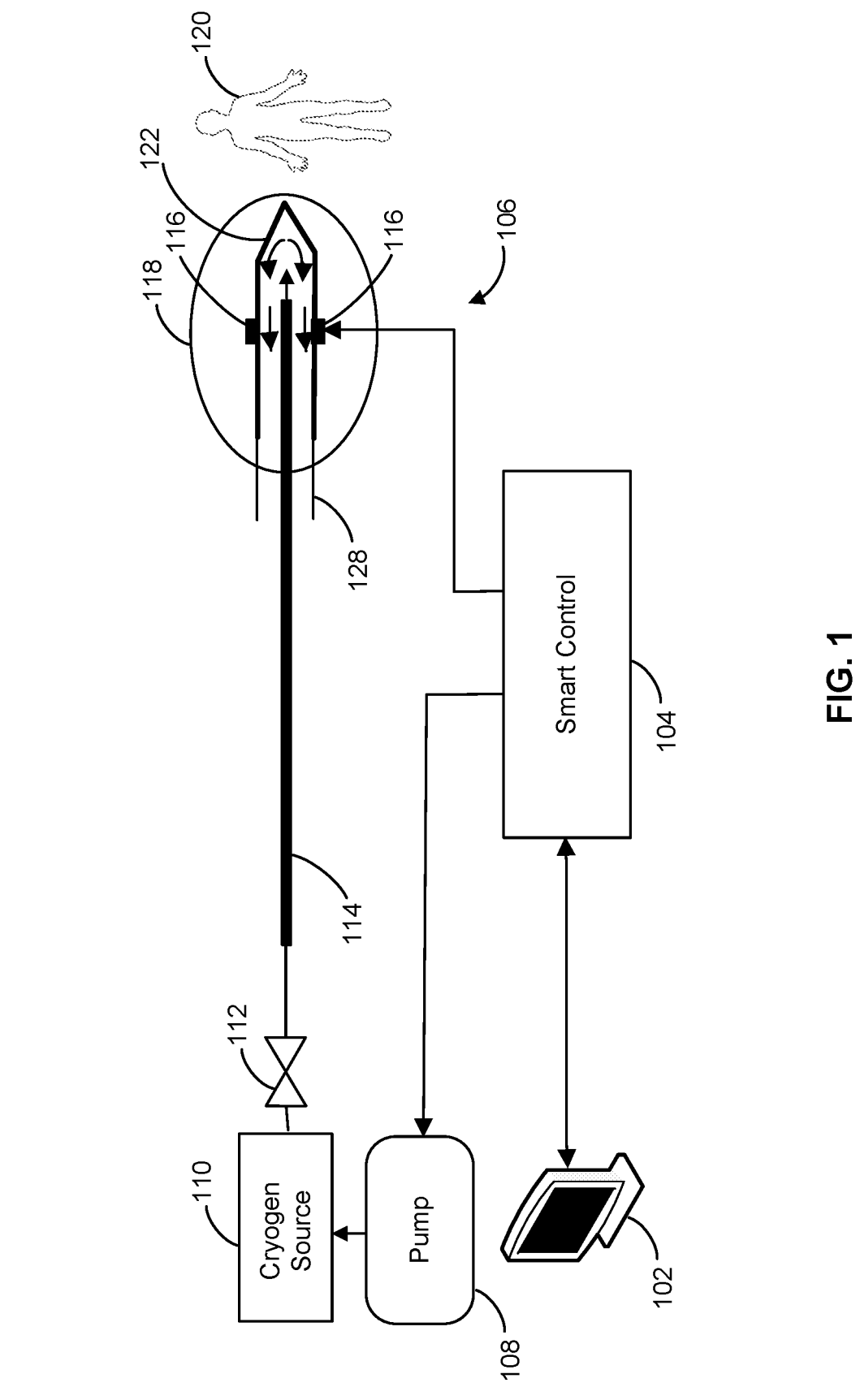
FIG. 1 is a diagram illustrating an example cryoablation system in accordance with some embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The apparatuses and methods of the present disclosure may be used in connection with a cryoablation apparatus in which a cryoablation probe may be inserted into a patient at or near the target tissue. When a suitable cryogen is passed to the probe, heat can be removed from the region proximate the cryoablation probe. Ice typically begins to form when sufficient heat is removed lowering the temperature of the target tissue and the region surrounding the cryoablation probe.

As can be appreciated, it is desirable to ensure that the entire target tissue (e.g., an entire tumor) is destroyed during the cryoablation treatment. To increase the likelihood that this occurs, it may be desirable form an iceball that corresponds to the shape of the target tissue. In some instances, the target tissue (e.g., a tumor) may have a substantially symmetrical shape such as a sphere. In other instances, however, the target tissue may have an irregular or asymmetrical shape. Existing or traditional apparatuses and methods often produce an iceball that is symmetrical about the cryoablation probe that produce the iceball. As such, existing or traditional systems cannot form asymmetrical ice formations that can correspond to irregular or asymmetrical target tissues.

This disadvantage of existing and traditional apparatuses and methods can result in several shortcomings. First, the traditional treatments may require an oversized iceball to be form in order to ensure that the target tissue is encapsulated in the iceball to effectively destroy the target tissue. The oversized iceball may, however, subject healthy tissue surrounding the target tissue to freezing temperatures that may have detrimental effects on the healthy tissue. Second, the iceball may be undersized to avoid subjecting healthy tissue to freezing conditions. Such an undersized iceball may result in regions of the target tissue not being destroyed during treatment. Still further, existing and traditional apparatuses and methods do not allow for the active control and shaping of ice in multiple directions during cryoablation treatments.

The apparatuses and methods of the present disclosure address these shortcoming by providing apparatuses and methods that can form ice in asymmetrical shapes during cryoablation procedures. The apparatuses and methods of the present disclosure can also actively monitor, control and shape ice during a cryoablation treatment. The apparatuses and methods of the present disclosure can energize one or more heating portions in a cryoablation probe while the cryoprobe is being actively cooled with a cryogen. Such control of the heating portions in the cryoablation probe can cause ice to be shaped in a desired manner to produce asymmetrical shapes and to form ice in a shape that corresponds to the target tissue and may avoid healthy tissues.

Referring now to FIG. 1, an example cryoablation system 100 is shown. The cryoablation system 100 may include a cryoablation computing device 102, a smart control 104, a plurality of measurement points 106, a pump 108, a cryogen source 110, an inlet valve 112, a cryogen supply 114, and a cryoprobe 128. The pump 108, the cryogen source 110, the inlet valve 112, the cryogen supply 114, and the cryoprobe 128 may operate to deliver a cryogen from the cryogen source 110 to the cryoprobe 128 to perform a cryoablation treatment. The cryogen (e.g., liquid nitrogen) can be stored in the cryogen source 110, such as a Dewar or other suitable container, and then delivered to the cryoprobe 128 via the cryogen supply 114. The cryogen may expand at a tip 122 of the cryoprobe 128 and cool the tip 122 of the cryoprobe 128 to a temperature at which the target tissue of a patient 120 begins to freeze forming an iceball 118.

The term iceball may be used in the present disclosure to describe various types of ice formations that may occur as a result of the cryoablation freezing cycle. While the term iceball may be used, it should be understood that the ice that is formed during the cryoablation treatment may have shapes other than a ball or sphere shape. The iceball may be elliptical, or have irregular or asymmetrical shapes that may be formed due to ice growth at different rates and to different extents in various directions from the cryoprobe 128.

The cryoprobe 128 can be positioned at or near a target tissue (e.g., a tumor) in the patient 120. In this manner, the target tissue can be frozen destroying the target tissue. One or more freezing cycles can be performed in order to destroy the target tissue. The iceball 118 may form at the target tissue in the patient 120 during the freezing cycle. It is desirable to control and form the iceball 118 in a predetermined manner so the iceball 118 forms to a desired size, shape and rate so that the target tissue is frozen in the iceball 118 for a desired period of time. It is also desirable to form the iceball 118 with the desired size, shape and rate so that healthy tissue or body structures near the target tissue are not harmed by the freezing cycle. It can be desirable, for example, to limit a size of the iceball 118 so that it does not form and freeze healthy tissue.

A treatment plan can be determined prior to the performance of the cryoablation treatment. The treatment plan can detail and/or describe the various steps of the process and various aspects of the treatment such as the types of equipment to be used, a positioning of the cryoprobe, temperatures of the cryoprobe, duration of freezing (and thaw cycles) as well as a quantity of cycles. The treatment plan may also include a size, location, shape, growth rate and duration of an iceball. The treatment plan may be determined by a medical professional and/or by others. As will be further described, the treatment plan can be determined using one or more of the ice formation models created using methods of the present disclosure.

In some examples, the cryoablation computing device 102 may determine or recommend a treatment plan after health, patient, and other information is input into the cryoablation computing device 102 or such information is retrieved or otherwise obtained by the cryoablation computing device 102. The cryoablation computing device 102 may any suitable computing device such as a workstation, computer, laptop, tablet, server or the like.

As further shown, the cryoablation system 100 includes the smart control 104 that may be coupled to the cryoablation computing device 102, to the heating portions 116 and to the pump 108. The smart control 104 may be any suitable controller, PLC, data acquisition unit, control unit or the like that can perform the operations described herein. In some examples, the cryoablation computing device 102 and the smart control 104 can be combined in a single device. In others, they may be separate devices as shown. The smart control 104 may operate to control one or more heating portions 116 on the cryoprobe 128. The heating portions 116 may be energized or de-energized to control a growth of the iceball 118. The heating portions 116 can be used, for example, to form an asymmetrical iceball 118.

The smart control 104 and/or the cryoablation computing device 102 may also obtain ice formation data or information. The ice formation information may include temperature, and size information for the iceball at various times during a freezing cycle. The ice formation information may be obtained from various measurements points. The ice formation information may provide temperature information at predetermined locations in order to provide information regarding the growth of the ice at the target tissue. The measurement points may include temperature sensors, thermocouples, thermistors, impedance sensors, and the like. Such measurement points may be incorporated into the cryoprobe 128 and/or into a separate measurement lead.

The ice formation information may also include imaging data. The imaging data can be obtained from imaging devices such as x-ray devices, CT scan devices, ultrasound devices, MRI devices and the like. The imaging data can provide an indication of a size and shape of the iceball 118 during various stages of the freezing cycle.

The smart control 104 may operate to obtain the ice formation information from measurement points and provide the information to the cryoablation computing device 102. The cryoablation computing device 102 may then perform various operations to determine characteristics of the ice being formed during a cryoablation treatment. In addition, the cryoablation computing device 102 may perform operations to adjust, change, modify or otherwise control the one or more operating parameters of the cryoablation system 100. In some examples, the cryoablation computing device 102 may adjust the flow of the cryogen provided from the cryogen source 110 to the cryoprobe 128. The cryoablation computing device 102 may be coupled to the pump 108. The pump 108 can be an adjustable, programmable, or otherwise controllable pump. The pump 108 may allow for the flow rate, flow volume, flow speed, pressure or other characteristic of the flow of cryogen to be modified, controlled or customized. In some examples, the pump 108 can operate to deliver the cryogen to the cryoprobe 128 in a pulsed manner using pulse width modulation (PWM). In such examples, the pump 108 can be controlled to deliver a flow of cryogen at a desired frequency, pulse width, pulse amplitude or other desired flow characteristic.

While not shown, the smart control 104 and/or the cryoablation computing device 102 may also be coupled to other information sources. The smart control 104 and/or the cryoablation computing device 102 may be coupled to a medical information database that may include information regarding the patient 120 and/or to other clinical treatment procedures and the like.

The apparatuses and methods of the present disclosure, including the cryoprobes further described below, are appli-cable to various cryoablation systems including variations to the cryoablation system 100 described above and other cryoablation systems. The cryoprobes of the the present disclosure and the related methods of use can be used, for example, in Joules Thompson (JT) cryoablation systems, liquid phase cooling cryoablation systems, mixed phase cooling cryoablation systems, supercritical phase cooling cryoablation systems, subcritical phase cooling cryoablation systems, and other cryoablation systems that may employ other types of cooling effects.

Figure 2:
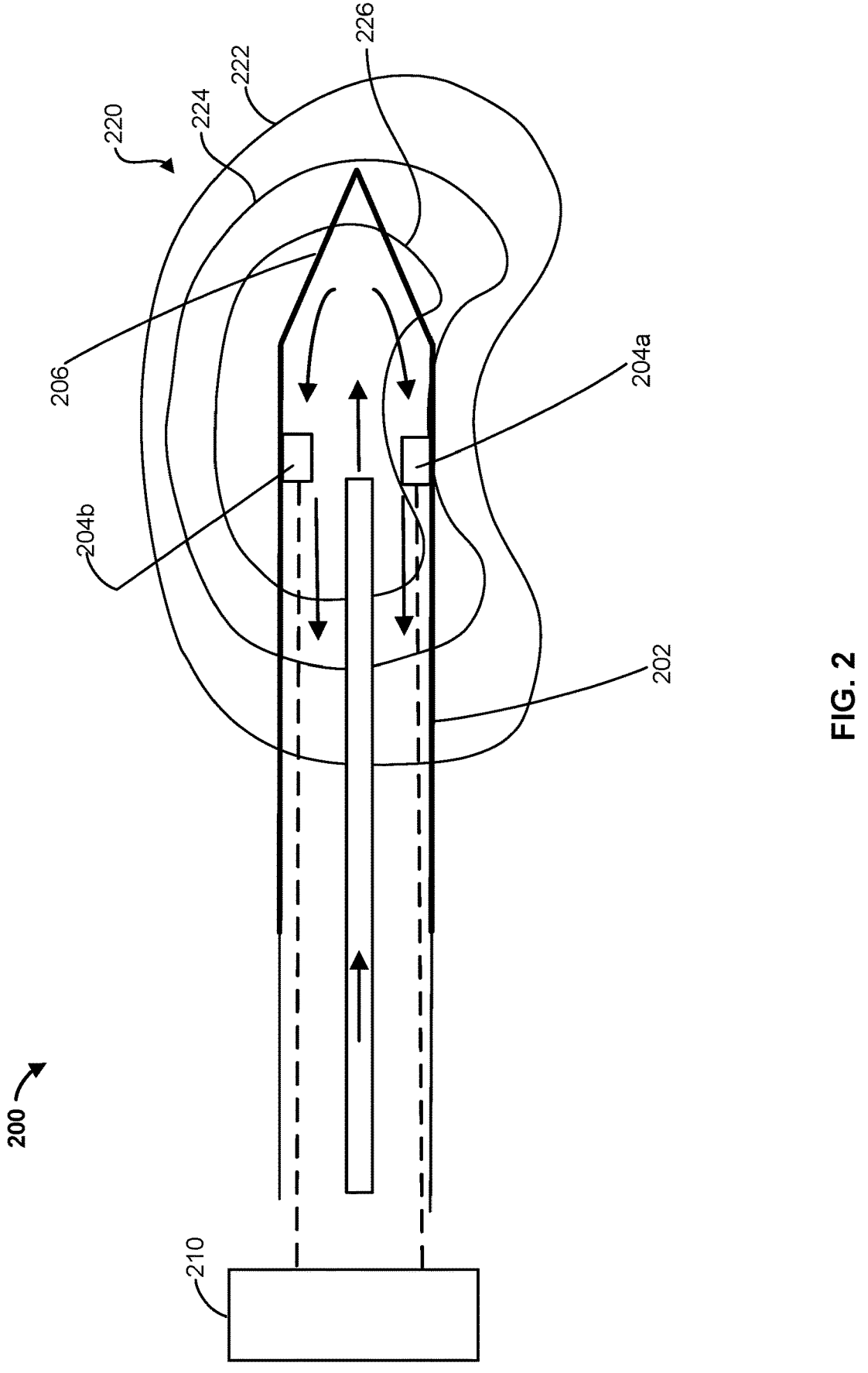
FIG. 2 is a diagram illustrating an example cryoprobe of the present disclosure that may form the illustrated asymmetrical iceball.

Referring now to FIG. 2, an example cryoprobe 200 is shown. The cryoprobe 200 may be used in the cryoablation system 100 previously described. The cryoprobe 200 can be used to ablate a target tissue during a freezing cycle of a cryoablation treatment. The cryoprobe 200 may include cryogen supply that is configured as a tube or other conduit to deliver cryogen from the cryogen source to the tip 206. The cryogen supply may be positioned along a center axis of the cryoprobe 200. A shell 202 may form the outer surface of the cryoprobe 200 and may be located radially outward of the cryogen supply. The cryogen may flow back from the tip 206 along a return path defined as the space between the interior surface of the shell 202 and the outer surface of the cryogen supply. The cryoprobe 200 may also include one or more heating portions 204 that can be positioned at various location circumferentially around the cryoprobe and at different longitudinal locations relative to the tip 206 of the cryoprobe 200. Each of the heating portions 204 can be coupled to a heating controller 210. The heating portions 204 can be coupled electrically via physical wired connections or via other connections.

In operation, the cryoprobe 200 is configured to remove heat from a target tissue of a patient. Such operation causes an iceball 220 to form at the target tissue. The iceball 220 can be formed with a suitable temperature to destroy the target tissue. The iceball 220 can be formed to have various temperature boundaries or isotherms. The example shown in FIG. 2 shows an iceball 220 having a first isotherm 222, a second isotherm 224, and a third isotherm 226. The first isotherm 222 can correspond to an outer edge of the iceball 220 that defines a 0° C. isotherm. The first isotherm 222 can correspond, for example, to a boundary at which the temperature of the ice has reached a temperature of 0° C. or lower. The second isotherm 224 can be positioned inward of the first isotherm 222. The second isotherm 224 can define a temperature boundary at which the ice has reached a temperature of −20° C. or lower. The third isotherm 226 can be positioned inward of the both the first isotherm 222 and the second isotherm 224. The third isotherm 226 can correspond to a temperature boundary at which the iceball 220 has reached a temperature of −40° C. or lower.

It is desirable to position the cryoprobe 200 and form the iceball 220 in a manner so that the second isotherm 224 and/or the third isotherm 226 are located around the target tissue. It has been observed that tissue is destroyed when subjected to a temperature of at least −20° C.

The heating controller 210 can be a suitable controllable power supply, PLC or computing device or combination thereof that can selectively deliver a power signal to the heating portions 204. The heating controller 210 can energize or de-energize each of the heating portions 204a and 204b independently of one another. The heating controller 210 can energize the heating portions 204a, 204b to cause the heating portions to generate heat. The heat generated from the heating portions 204a, 204b can, in turn, limit the growth of ice in a region proximate to the heating portion 204a and/or 204b.

When the cryogen is dispensed to the cryoprobe 200 and expands at the tip 206, the temperature of the cryogen (e.g., liquid nitrogen) lowers and causes ice to form at the cryoprobe 200. Such ice may typically form symmetrically about the cryoprobe 200, at least symmetrically about a center axis of the cryoprobe 200. As such, the iceball 220 may form in the shape of sphere or an ellipsoid. It may be desirable, however, to limit the growth of ice in one or more directions relative to the center axis of the cryoprobe 208. To limit growth, the heating controller 210 may energize one or more of the heating portions 204a, 204b.

In the example shown, the iceball 220 has an asymmetrical shape. To achieve the shape shown, the heating controller may have energized the heating portion 204a (shown on a lower portion on the cryoprobe 208). The heating portion may generate heat via a resistive heater, microwave antenna, radio frequency (RF) heater, laser heater or the like. The heat may reduce the amount of heat that is extracted by the probe via the cryogen in a local region proximate to the heating portion 204a. Similarly, the heating controller 210 may energize the heating portion 204b to limit the growth of heat at an upper region of the cryoprobe 200.

The heating controller 210 may energize or actuate the heating portions 204a, 204b selectively, independently, and variably to control the growth of ice. The heating controller 210 may control the formation of ice so that the iceball 220 forms to a size, shape, and/or temperature so that the iceball 220, including the first isotherm 222, the second isotherm 224, and the third isotherm 226, correspond to a location, size and shape of the target tissue (e.g, tumor). The heating controller 210 may also control the formation of ice so that the size, shape, location, and/or temperature of the iceball 220 minimizes or reduces detrimental effects of the ice on healthy tissues that maybe located proximate to the target tissue.

As shown in FIG. 3, another example cryoprobe 300 may include four heating portions 304a, 304b, 304c, 304d. The heating portions 304 may be located and positioned circumferentially around a center of the cryoprobe 300. The heating portions 304 may be evenly spaced around an outer surface 302 of the cryoprobe 300. In the example shown, the heating portions are positioned at 90 degree intervals around the circumference of the cryoprobe 300. As previously discussed, the heating portions 304 can be independently, selectively and variably actuated or energized to heat a local region when ice is forming at the target tissue to locally limit the growth of ice and form asymmetrical iceballs.

The heating portions 304 can be configured in various manners, including as resistive heaters, RF heaters, laser heaters or the like. In one example shown in FIG. 4, a heating portion 400 may be configured as a resistive heater in which a resistive wire 404 can be routed in a heater body 402. The resistive wire can be routed in longitudinal wrappings through the heater body 402.

In an alternate example as shown in FIG. 5, a heating portion 500 can also include a resistive wire 504 routed through a heater body 502. The resistive wire 504, in this example, can be routed in lateral wrappings through the heater body. As can be appreciated, the heating portion can also be configured to have other structures to provide localized heating in the cryoprobe.

Figures 6, 7, 8:
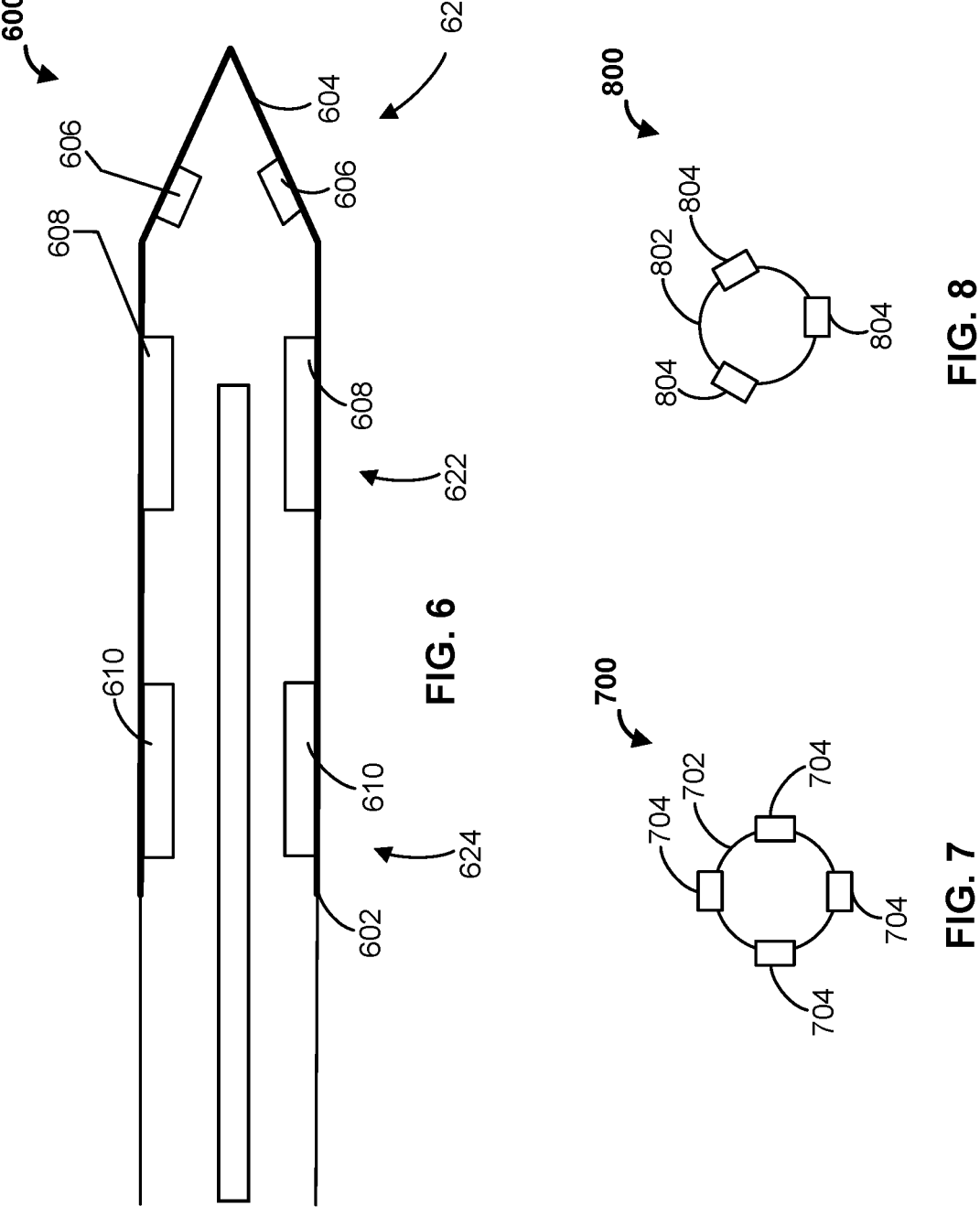
FIG. 6 is a side view of another example cryoprobe that includes three heating portion arrays.
FIG. 7 is a cross-sectional view of another example cryoprobe of the present disclosure.
FIG. 8 is a cross-sectional view of another example cryoprobe of the present disclosure.

The cryoprobe may also be configured to have multiple arrays of heating portions that can be located at different longitudinal locations relative to the tip of the cryoprobe. One such example is shown in FIG. 6. As shown, the cryoprobe 600 may include a first heating array 620 that includes multiple heating portions 606 located around a circumference of the cryoprobe 600. The cryoprobe 600 may also include a second heating array 622. The second heating array 622 may also include multiple heating portions 608 located around the circumference of the shell 602 of the cryoprobe 600. The second heating array 622 is located at a position further away from the tip 604 than the first heating array 620. The cryoprobe 600 may also include a third heating array 624 positioned still further away from the tip 604. The third heating array 624 can include multiple heating portions 610 located around a circumference of the shell 602.

The heating portions of each heating array can be operated independently, selectively, and variably as previously described to enable the control and shaping of the iceball. While not shown, each of the heating portions of the first heating array 620, the second heating array 622, and the third heating array 624 can be individually coupled to a heating controller to provide the operation and control as previously described.

Each of the heating portions 606, 608, 610 of the first heating array 620, the second heating array 622, and the third heating array 624, respectively, can be positioned in any desirable configuration around the shell 602 of the cryoprobe 600. FIGS. 7 and 8 show two example configurations of the cryoprobe 600 at one or more cross-sections. As shown, in FIG. 7, the cross-section 700 may include four heating portions 704 positioned evenly at about 90 degree intervals around the cryoprobe. As shown in FIG. 8, the cross-section 800 may include three heating portions 804 positioned around a shell 802 of the cryoprobe. Each heating array may include the same spacing and number of heating portions or the various heating arrays may have different spacing and number of heating portions. In still other examples not shown, the heating portions have different spacing and each array can include more than four heating portions or less than three heating portions.

Figure 9:
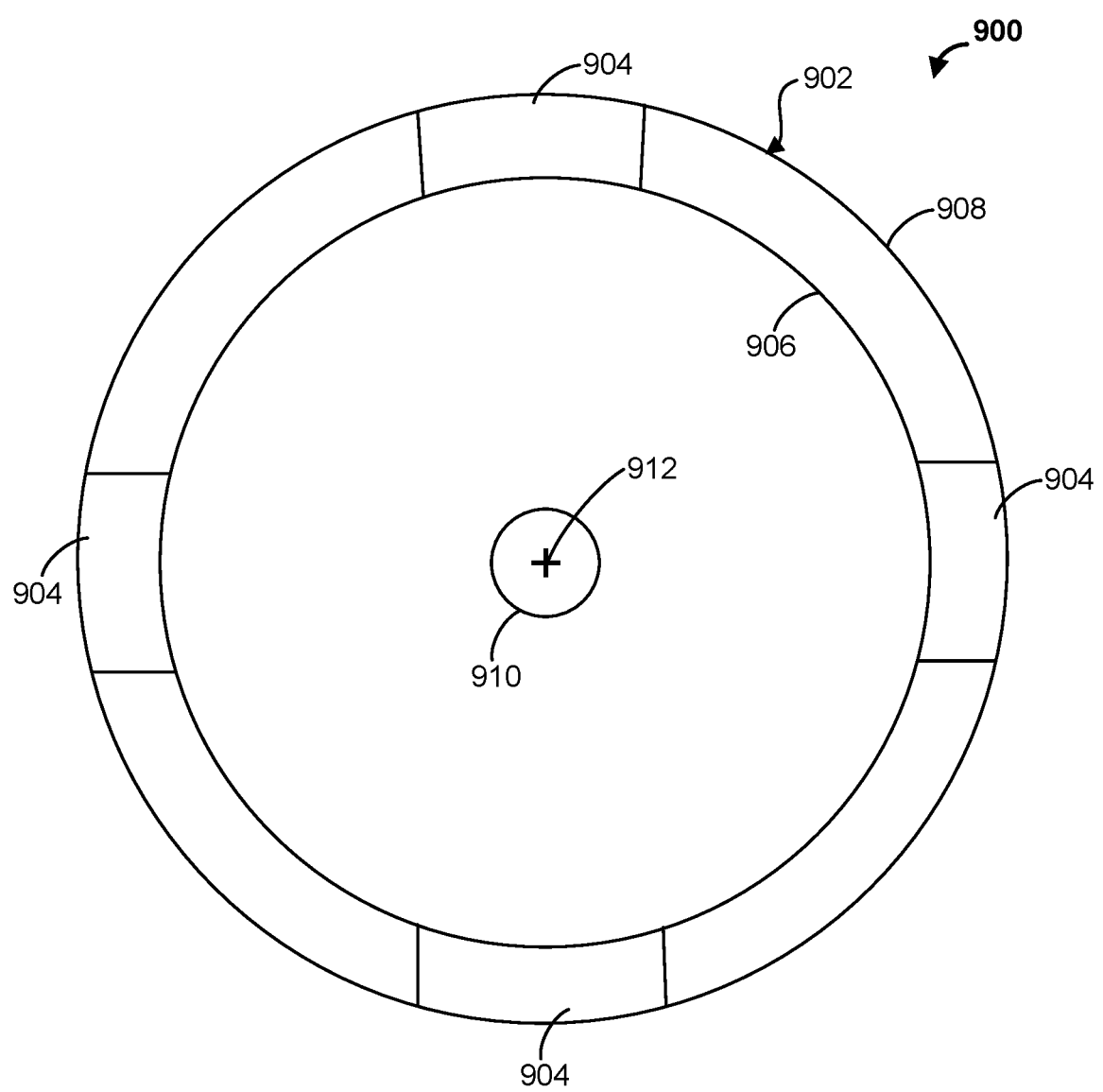
FIG. 9 is a cross-sectional view of another example cryoprobe of the present disclosure.

Still another cross-section 900 is shown in FIG. 9. In this example, the cross-section 900 shows the cryogen supply 910 positioned at the center about the central axis 912 of the cryoprobe. In this example, the heating portions 904 are positioned at intervals within the shell 902 of the cryoprobe. As can be seen, the heating portions can be embedded in the shell 902 such that the heating portions 904 do not extend radially inward of the inner surface 906 of the shell 902. The heating portions 904 may also not extend radially outward of the outer surface 908 of the shell 902. The shell 902 of the cryoprobe 900 may be formed to have such a structure in various manners. In one example, the shell 902 may be formed using 3D printing or additive manufacturing processes to embed the heater structure in the shell 902. For example, the resistive wire can be deposited as one material and the heater body can be deposited as another material during construction of the cryoprobe. In other examples, other process and techniques can be used to construct the cryoprobe 900.

The previously described cryoprobes and/or heating portions can be used in connection with various cryoablation processes and systems that may use one or more types of cooling to form ice at the target tissue. The cryoprobes and/or heating portions and heating arrays can be used in cryoprobes that utilize Joules Thompson cooling, liquid phase cooling, mixed phase cooling, super critical phase cooling, subcritical phase cooling, and/or other cooling processes.

Figure 10:
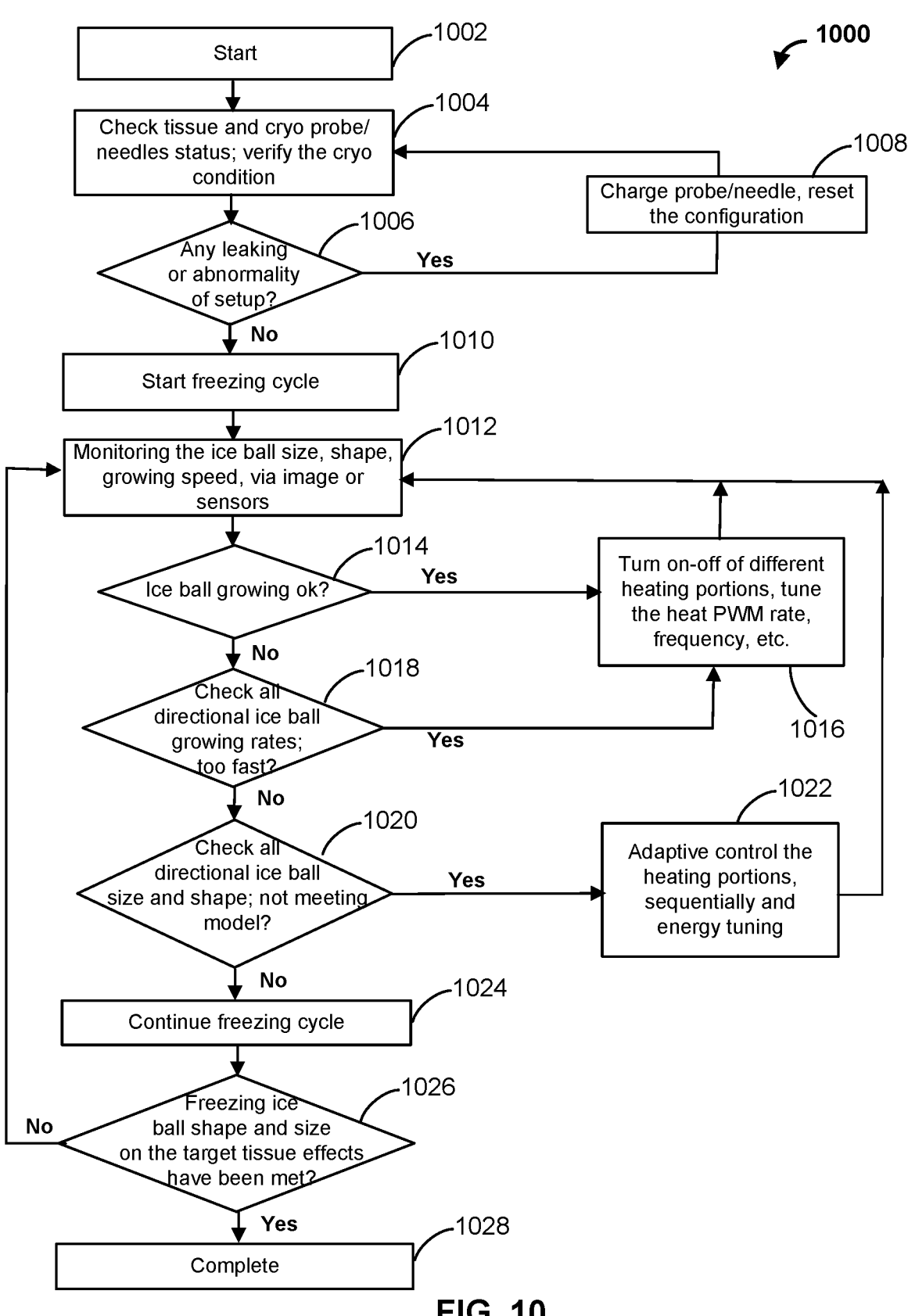
FIG. 10 is a flow chart illustrating an example method of forming an asymmetrical ice formation during a cryoablation treatment.

Referring now to FIG. 10, an example method 1000 of performing a cryoablation treatment is shown. The method 1000 can be performed using the cryoablation system 100 in some embodiments. The method 1000 can also be performed using other cryoablation systems. For the sake of brevity, the method 1000 is described with reference to the cryoablation system 1000. It should be appreciated, however, that other cryoablation apparatuses and system can also be used.

The method 1000 begins at step 1002. At step 1002, the cryoablation computing device 102 may start the process of a cryoablation treatment. The cryoablation computing device 102 may, for example, obtain pre-set conditions or obtain other data that characterizes the treatment that is to be performed. The cryoablation computing device 102 may obtain such information automatically or the information may be input by a medical professional.

The method 100 may then proceed to step 1004. At step 1004, the cryoablation computing device 102 may check a status of the cryoablation system 100 including a status and/or location of the cryoprobe 128. The cryoablation computing device 102 may also verify the operating conditions of the cryoablation system. The cryoablation computing device 102 may perform step 1004 by obtaining data or information from measurement points, imaging systems, sensors or other diagnostic devices that may provide such information to the cryoablation computing device 102.

At step 1006, the cryoablation computing device may determine whether an abnormality or other issue (e.g. leaking) may be occurring. The cryoablation computing device 102 may determine whether an abnormality exists by comparing the operating conditions of the cryoablation system 100 to predetermined stored values or start-up conditions that may be retrieved from a database or other treatment materials. If an abnormality is detected, the method 1000 may proceed to step 1008. At step 1008, the cryoablation computing device 102 deliver a message or other indication to a user of the cryoablation system 100. In response, the medical professional or other user may change a position of the cryoprobe 128 and/or revise or correct the treatment apparatus. The method may return to step 1004 after step 1008.

If the cryoablation computing device 102 determines that no abnormality exists, the method 1000 may proceed to step 1010. At step 1010, the freezing cycle of the cryoablation treatment may start. To begin the freezing cycle, the cryoablation computing device 102 may initiate the flow of cryogen to the tip of the cryoprobe 128. The flow of cryogen may be initiated using one or more pre-set operating conditions that may characterize a pressure, flow, flow rate, temperature or other parameter of the cryoablation system 100.

The method 1000 may then proceed to step 1012. At step 1012, the cryoablation computing device 102 may monitor the size, shape, growth and other characteristics of the iceball that forms at the cryoprobe 128. The cryoablation computing device 102 may, for example, obtain ice formation data that characterizes the size, shape, temperature, and other characteristics of the iceball. The cryoablation computing device 102 may obtain ice formation data from imaging devices, temperature sensors, impedance sensors, or other data sources.

At step 1014, the cryoablation computing device 102 may determine whether the iceball is growing as desired. In some examples, the cryoablation computing device 102 may compare the ice formation data to one the treatment plan and/or to an ice formation profile. The cryoablation computing device 102 may compare a size, location, growing rate, temperature or other information to target information or to threshold information. The predetermined targets and/or thresholds may be obtained from an ice formation model in some examples.

If the iceball is not growing as desired, the method may proceed to step 1016. At step 1016, the cryoablation computing device may perform operations to adjust, change, or modify the growth of the iceball. Such operations may include energizing or de-energizing heating portions of the cryoprobe 128. The cryoablation computing device may also tune the power that is delivered to the heating portions and/or energize the heating portion according a predetermined power profile that may include a pulse width modulated (PWM) profile or may have a desired frequency or other characteristic. Such action may cause heat to be generated at a local region at the cryoprobe 128 to cause the iceball growth to change. After step 1016, the method 1000 may return to step 1012 to re-perform steps 1012, 1014 as previously described.

If the iceball is growing as desired, the method 1000 may proceed to step 1018. At step 1018, the cryoablation computing device 102 may check all directions of iceball growth to determine whether the iceball is growing too fast in any direction. Various directions may be established so that the cryoablation computing device 102 may determine growth characteristics of the iceball along different directions from the cryoprobe 128. Since the cryoablation systems of the present disclosure can cause iceballs to be grown that have asymmetric profiles, the iceball may grow at different rates along different directions from a predetermined location on the cryoprobe 128. Thus, the cryoablation computing device can obtain ice formation data for different directions from a common point on the cryoprobe 128.

By monitoring the size, shape, location, temperature and/or other characteristics of the iceball during the freezing cycle, the cryoablation computing device can compare the growth rate of the iceball to a predicted or predetermined growth rate. If the cryoablation computing device 102 determines that the iceball is growing too quickly in one or more directions, the method 1000 may proceed to step 1016. At step 1016, the cryoablation computing device 102 may perform operations to adjust, change and/or reduce the growth of ice in the direction where it is has been identified as growing too quickly. In such a circumstance, the cryoablation computing device 102 may energize, adjust, or tune the power being delivered to the heating portion on the cryoprobe 128 that is located in the corresponding location. For example, if a top portion of the iceball is determined to be growing too quickly, the cryoablation computing device 102 may energize the heating portion located on a top portion of the cryoprobe 128 to generate heat and slow the growth of ice in this region.

If the cryoablation computing device 102 determines that the iceball is not growing too quickly in any direction, the method 1000 may proceed to step 1020. At step 1020, the cryoablation computing device 102 determine whether a size or shape of the iceball meets corresponds to desired iceball size and shape. A desired iceball size and shape may be determined when a treatment plan is determined in some examples. The treatment plan may, for example, describe the overall size and shape of the iceball that is to be created during the freezing cycle. The overall size and shape may be determined, for example, to correspond to a size and shape of the target tissue (e.g., tumor) that is desired to be destroyed. The overall size and shape of the iceball in the treatment plan may also be determined by avoiding healthy tissues or body structures that are located proximate to the target tissue in the patient. The overall size and shape of the iceball in the treatment plan may have an asymmetrical shape. That is, the outer edge may have a different distance or radius from a common point on the cryoprobe 128 in one or more directions.

The cryoablation computing device 102 may compare the overall size and shape of the iceball that is formed during the freezing cycle to the overall size and shape of the desired iceball of the treatment plan. The cryoablation computing device 102 may compare, for example, imaging data that characterizes the size, shape, and location of the iceball to the desired size, shape, and location of the treatment plan. The size, shape, and location of the iceball may be compared at various intervals during the freezing cycle.

If the size, shape, and location of the iceball does not correspond to the desired size, shape, and location of the iceball, the method 1000 may proceed to step 1022. At step 1022, the cryoablation computing device 102 may perform operations to adjust, change, and/or modify the size, shape, and location of the iceball. The cryoablation computing device 102 may energize, de-energize, or modify a power level/profile to one or more heating portions of the cryoprobe 128.

If the size, shape, and location of the iceball corresponds to the desired size, shape, and location, the method 1000 may proceed to step 1024. At step 1024, the cryoablation computing device 102 can continue the freezing cycle. The cryoablation computing device 102 can continue to cause the cryogen to flow to the cryoprobe 128 and can continue to energize, de-energize and/or otherwise operate the heating portions of the cryoprobe to grow and size the iceball in a desired size, shape and location.

At step 1026, the cryoablation computing device 102 can determine whether the iceball has achieved a desired size, shape, location and/or time duration relative to the target tissue. The final or overall size, shape, location and/or duration can be described in the treatment plan. The cryoablation computing device 102 can compare the size, shape, location and/or duration to the details of the treatment plan. If the size, shape, location and/or duration of the iceball does not meet the requirements as described in the treatment plan or other treatment specification, the method returns to step 1012 to re-perform the steps 1012 through 1026. If the size, shape, location and/or duration of the iceball meets the requirements, the method 1000 may proceed to step 1028 at which time the method may be completed. As can be appreciated, the method 1000 may be followed by a thaw process or may be re-performed if the cryoablation treatment includes multiple freezing cycles.

Figure 11:
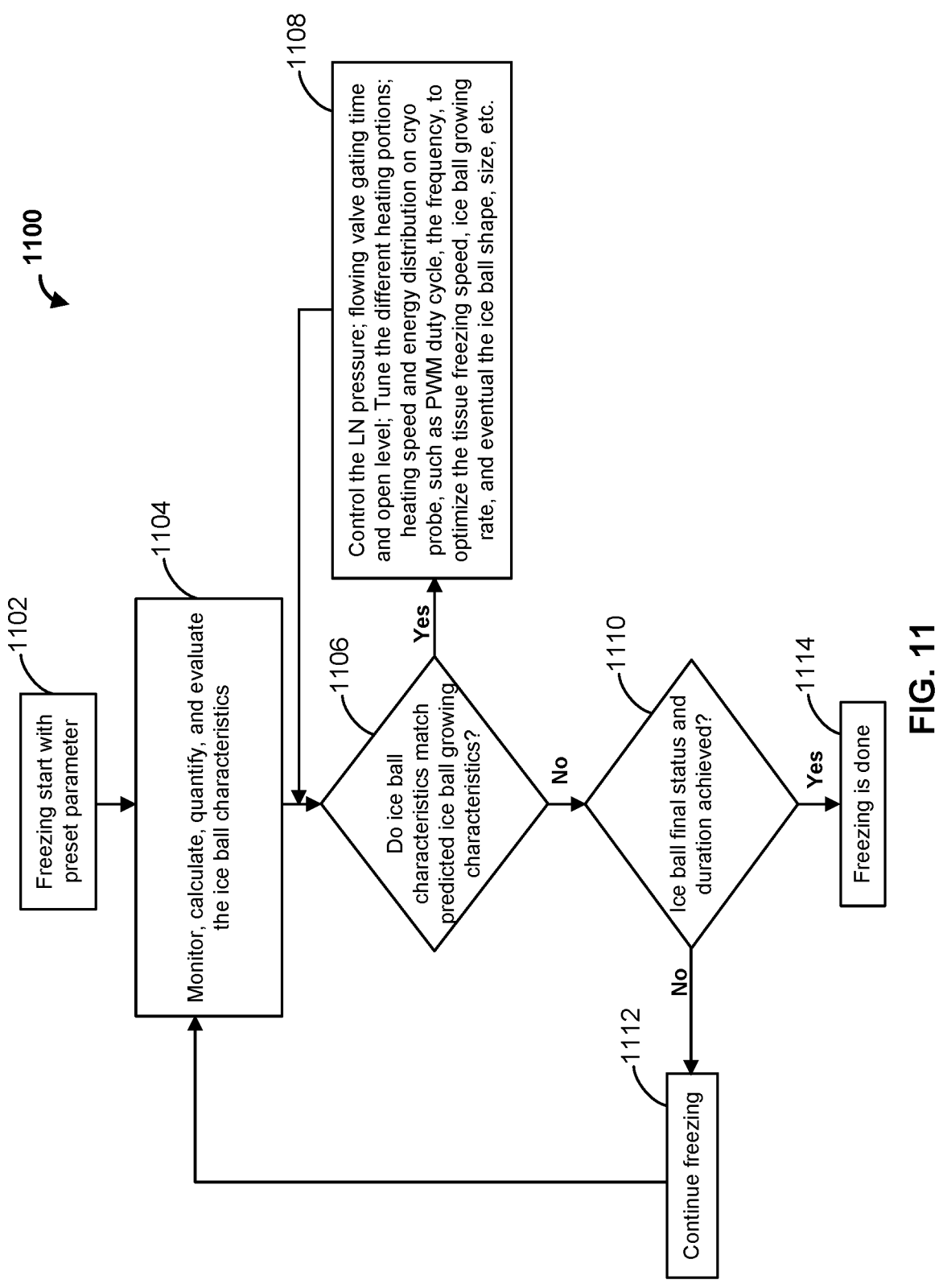
FIG. 11 is a flow chart illustrating another example method of forming an asymmetrical ice formation during a cryoablation treatment.

Referring now to FIG. 11, another method 1100 of performing a cryoablation treatment is provided. The method 1100 may be performed by the cryoablation apparatus 100. In other examples, other cryoablation apparatuses can be used. For the sake of brevity, the method 1100 is described with reference to the apparatus 1100. It should be appreciated, however, that other apparatuses and/or systems can also be used.

The method 1100 is similar in some respects to the method 1000 previously described. The method 1100 may incorporate the use of an ice formation model. The ice formation model may predict the growth of the ice during a freezing cycle of a cryoablation treatment based on tissue type, tissue location, patient information, operating conditions of the cryoablation apparatus and/or other factors. In some examples, an affine ice formation model is used that may be constructed to predict the growth of ice in multiple directions from a predetermined point on the cryoprobe 128. In other examples, other ice formation models can be used.

At step 1102, the freezing cycle of a cryoablation treatment may begin. The cryoablation computing device 102 may, for example, initiate a flow of cryogen to the cryoprobe 128. The cryoablation computing device 102 may initiate the flow using one or more preset operating conditions of the cryoablation system 100. Such preset operating conditions may, for example, describe a flow rate, pressure, temperature, and/or other parameters of the cryogen. The preset operating conditions may also describe an operating condition of the heating portions of the cryoprobe 128. One or more of the heating portions may be energized to heat a region of the cryoprobe 128 to effect a growth of the iceball in a localized region.

The method 1100 may proceed to step 1104. At step 1104, the cryoablation computing device 102 may monitor, calculate, quantify, and/or evaluate the iceball that is forming at the target tissue. The cryoablation computing device 102 may obtain ice formation information that may describe a size, location, temperature and other characteristics of the iceball that is forming at the target tissue. The cryoablation computing device 102 may obtain such information from any suitable data source such as a database, imaging devices, temperature sensors, impedance sensors or the like.

At step 1106, the cryoablation computing device 102 may determine whether the iceball growing characteristics match predicted iceball growing characteristics of an ice formation model. The cryoablation computing device 102 may compare the ice formation information that is obtained at step 1104 to corresponding characteristics of the ice formation model. For example, the iceball growing rate, iceball size, iceball location and the like may be compared to corresponding predicted growth rates, sizes and locations that are predicted by the ice formation model. The cryoablation computing device 102 may compare such characteristics to predetermined thresholds or predetermined ranges that may be provided or obtained from the ice formation model. If the cryoablation computing device determines that the iceball growing characteristics do not match the predicted ice growing characteristics, the method 1100 may proceed to step 1108.

At step 1108, the cryoablation computing device 102 may energize or other adjust, or modify the operation of one or more heating portions that are located on the cryoprobe 128. The cryoablation computing device 102 may energize a heating portion that is located at a position on the cryoprobe 128 that corresponds to the location at which the iceball growing characteristic does not match the predicted growing characteristic. In other examples, the cryoablation computing device 102 may adjust a duty cycle that is provided to one or more heating portions. As such the energy distribution to the heating portion(s) can be modified as needed to change the growth of ice in a localized region. The cryoablation computing device 102 may also change, modify or adjust other operating characteristics of the cryoablation system 100 such as the pressure, flow, flow rate, temperature or other parameter of the cryogen being provided to the cryoprobe 128. After step 1108 is performed, the method 1100 may return to step 1106 to re-perform the operations described above.

If the cryoablation computing device 102 determines that the iceball growing characteristics match the predicted growth characteristics, the method 1100 can proceed from steps 1106 to step 1110. At step 1110, the cryoablation computing device 102 can determine whether a final iceball growth status and duration has been achieved. As previously described, the freezing cycles of cryoablation treatments often describe a desired final size of the iceball to correspond to the target tissue and a duration at which the final size of the iceball is maintained to destroy the target tissue. The cryoablation computing device 102 may compare the size, shape, location and duration to the desired iceball final characteristics. If the iceball has achieved the desired final size, shape, location and duration, the method 1100 may proceed to step 1114 at which the freezing cycle is completed.

If the iceball has not achieved the desired final size, shape, location and duration, the method 1100 may proceed to step 1112. At step 1112, the cryoablation computing device may maintain an operating condition of the cryoablation system 100 and continue the freezing cycle. The method 1100 may then return to step 1104 to re-perform the steps 1104 to 1110 as previously described until such time when the cryoablation computing device determines the final iceball characteristics are achieved.

The method 1100 describes a freezing cycle of a cryoablation treatment. As can be appreciated, the method 1100 may be followed by a thaw cycle or may be re-performed for a second, third or other further times as may be defined in the treatment plan. The method 1100 is an improvement over traditional and existing systems in that the control and operation of the various heating portions on the cryoprobe may allow the cryoablation computing device 102 to control, shape, and grow iceballs that have asymmetric shapes.

Figure 12:
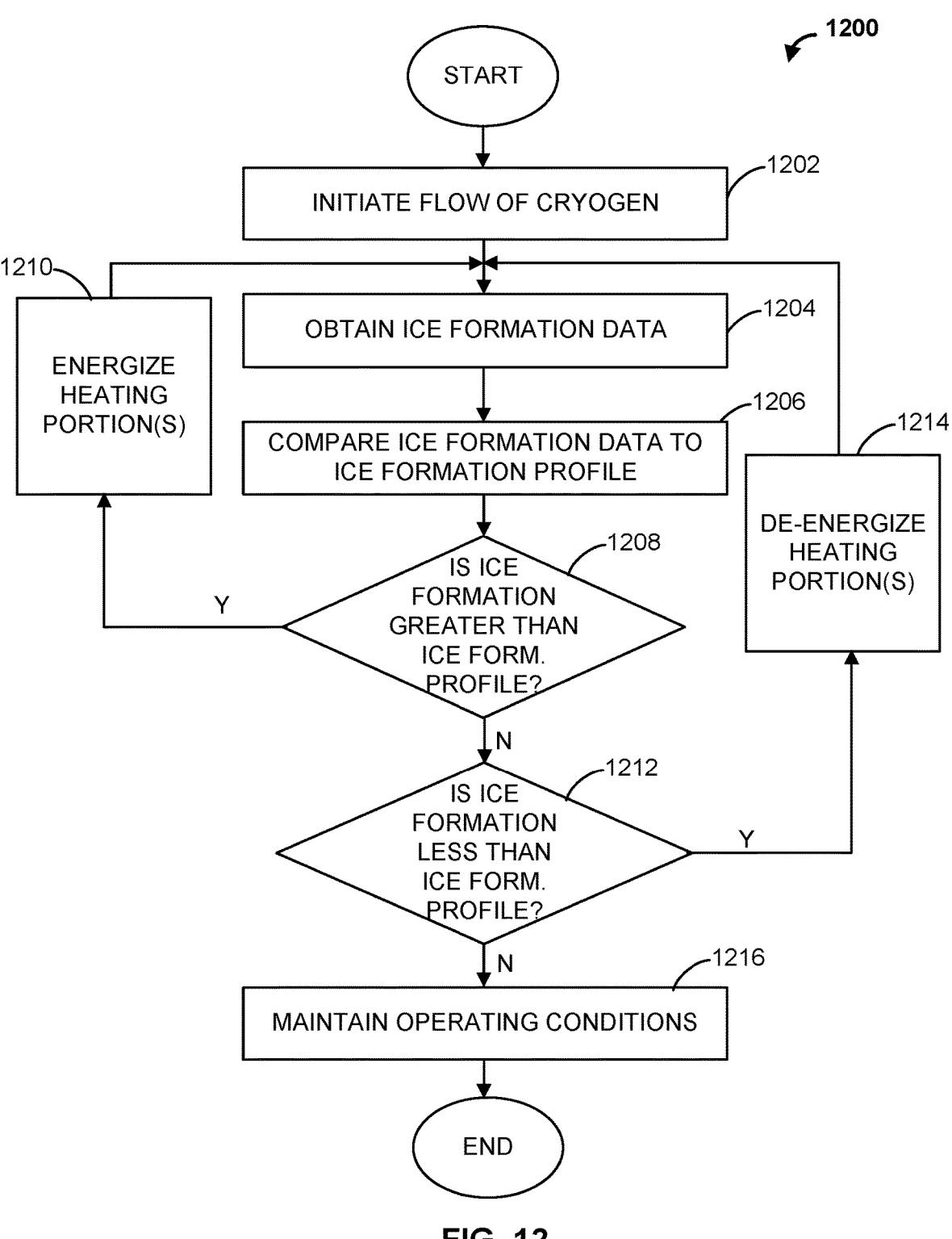
FIG. 12 is a flow chart illustrating another example of forming an asymmetrical ice formation during a cryoablation treatment.

Referring now to FIG. 12, another example method 1200 of performing a cryoablation treatment is shown. The method 1200 may be used to perform a freezing cycle and to grow an iceball having an asymmetrical shape. The method 1200 may be performed using various cryoablation apparatuses and systems, such as the cryoablation system 100. For the sake of brevity, the method 1200 is described with reference to cryoablation system 100. It should be appreciated, however, that other cryoablation apparatuses and systems can also be used.

The method 1200 begins with step 1202. At step 1202, the cryoablation computing device 102 may initiate a flow of cryogen. The flow of cryogen can be initiated, for example, by opening a valve and causing the cryogen to flow to the tip of the cryoprobe 128 to cool the tip and begin the formation of ice. While not shown, the cryoprobe 128 was positioned in a predetermined location at the target tissue. The location as well as other start-up information (e.g., initial operating parameters of the cryoablation system 100) may be included as part of a treatment plan that can be obtained by the cryoablation computing device 102. In other examples, a medical professional or other user may input start-up information into the cryoablation computing device 102.

The method 1200 may then proceed to step 1204. At step 1204, the cryoablation computing device 102 may obtain ice formation data. The ice formation data may describe various characteristics of the iceball that is forming at the target tissue. The ice formation data may be obtained, for example, from imaging devices, sensors, temperature sensors, impedance sensors, and the like. The ice formation data may characterize a size, temperature, shape, location and other characteristics of the iceball.

At step 1206, the cryoablation computing device 102 may compare the ice formation data to an ice formation profile. The ice formation profile may be provided with or using an ice formation model. The ice formation profile may predict various aspects of an iceball. The ice formation profile may, for example, predict a size, shape, location, growth rate, temperature and other characteristics of the iceball at various intervals during a freezing cycle. For each characteristic, a target threshold or target range may be provided. The cryoablation computing device 102 may compare the ice formation data that characterizes the actual iceball being formed to the ice formation profile at step 1206.

At step 1208, the cryoablation computing device 102 may determine whether one or more characteristics of the actual ice being formed is greater than one or more corresponding characteristics described in the ice formation profile. The cryoablation computing device 102 may compare a value for one or more characteristics to a predetermined threshold or to a predetermined range. If the value is greater than the predetermined threshold or predetermined range, it may indicate that the ice is growing too quickly or has already grown too quickly. If the cryoablation computing device 102 determines that such a condition is present, the method 1200 may proceed to step 1210.

At step 1210, the cryoablation computing device may energize a heating portion. The heating portion may create heat than can reduce the growth of ice and/or slow a growth of ice in a desired location. In other examples, the cryoablation computing device may increase a power level to the heating portion and/or change a duty cycle that is being delivered to the heating portion. The cryoablation computing device 102 may take any suitable action to reduce or slow the growth of ice in a desired location. After such action is performed, the method 1200 may return to step 1204 and re-perform the steps 1204 to 1208.

If the cryoablation computing device 102 determines that the ice forming during the freezing cycle is not greater than the ice formation profile, the method 1200 proceeds to step 1212. At step 1212, the cryoablation computing device determines whether the ice formation data indicates that ice growth is less than that described in the ice formation profile. The cryoablation computing device 102 may perform operations similarly to that previously described at step 1208 except that the cryoablation computing device determines if the ice growth is slower than predicted or the iceball has a smaller size than that predicted by the ice formation profile. If the cryoablation computing device determines that the ice formation is smaller or has a slower growth rate than that predicted, the method 1200 may proceed to step 1214.

At step 1214, the cryoablation computing device 102 may adjust, change or de-energize one or more heating portions on the cryoprobe 128. Since the cryoablation computing device has determined that the ice is smaller or is growing slower than that predicted or anticipated, the heat being introduced by the heating portions needs to be reduced. To accomplish this, the cryoablation computing device can de-energize the heating portion, change a power level delivered to the heating portions and/or modify a duty cycle being delivered to the heating portion. The cryoablation computing device 102 may also modify other operating parameters of the cryoablation system 100 such as modifying the pressure, temperature, flow, flow rate or other characteristic of the cryogen. After such operations are performed, the method 1200 may return to re-perform steps 1204 to 1212.

If the cryoablation computing device 102 determines that the ice formation is not less than that described in the ice formation profile, the method may proceed to step 1216 at which time the operating conditions of the cryoablation system 100 are maintained until the ice is formed to a desired size, location, shape and duration. After step 1216, the freezing cycle may end.

As can be appreciated, the method 1200 can be re-performed if a treatment plan calls for multiple freezing cycles or the method 1200 may be followed by a thaw cycle. The method 1200 allows the cryoablation computing device to monitor, control and adjust for the growth of ice in multiple directions to allow an asymmetrical iceball to be formed at the target tissue. The location of the heating portions on the cryoprobe 128 as previously described can be energized, de-energized, or otherwise controlled to effect ice growth at localized regions around the cryoprobe. Such control is an improvement over existing and traditional systems.

Figure 13:
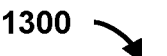
FIG. 13 is a diagram illustrating an example computing device that can be used in connection with the apparatuses and methods of the present disclosure.
Figure 13:
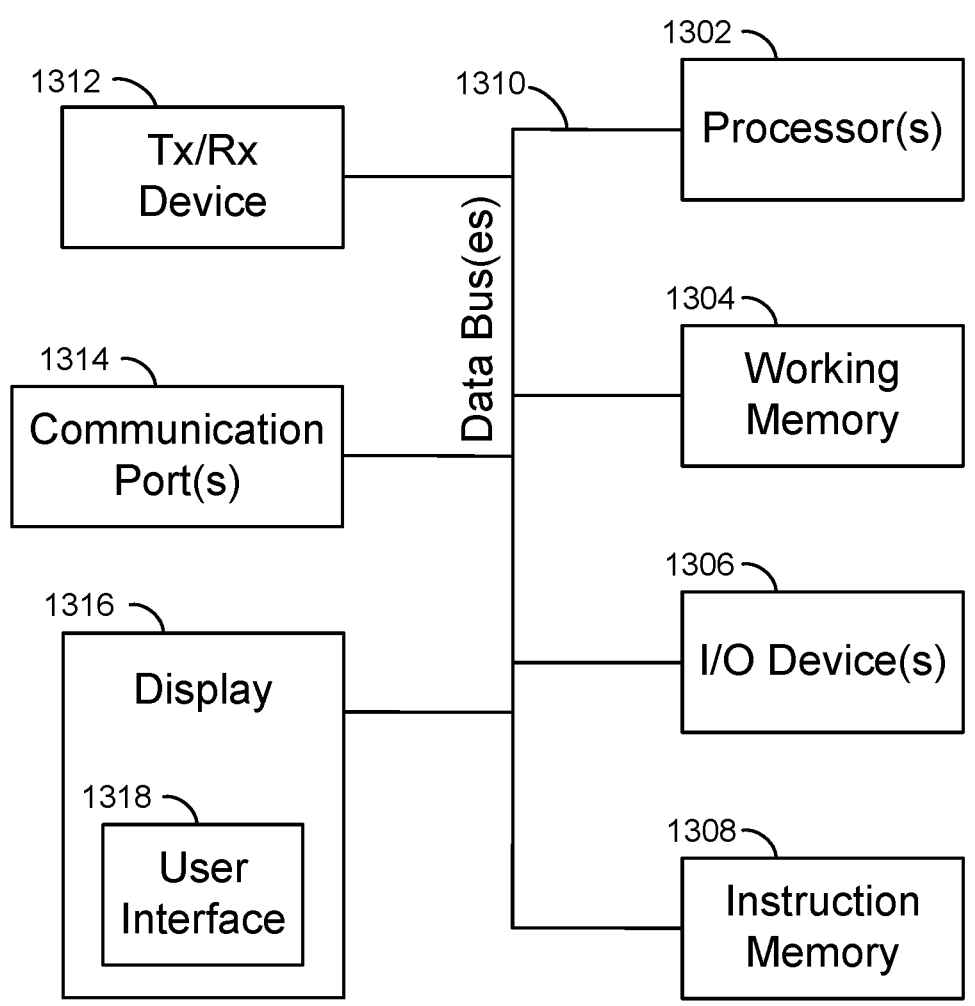

Referring now to FIG. 13, an example computing device 1300 is shown. The cryoablation system 100 may include one or more computing devices 1300. For example, the cryoablation computing device 102 may have the elements shown in FIG. 13. The methods of the present disclosure, such as methods 1000, 1100, and 1200, may be performed, or steps of such methods may be performed, by a computing device 1300.

As shown, the computing device 1300 may include one or more processors 1302, working memory 1304, one or more input/output devices 1306, instruction memory 1308, a transceiver 1312, one or more communication ports 1314, and a display 1316, all operatively coupled to one or more data buses 1310. Data buses 1310 allow for communication among the various devices. Data buses 1310 can include wired, or wireless, communication channels.

Processors 1302 can include one or more distinct processors, each having one or more cores. Each of the distinct processors can have the same or different structure. Processors 1302 can include one or more central processing units (CPUs), one or more graphics processing units (GPUs), application specific integrated circuits (ASICs), digital signal processors (DSPs), and the like.

Processors 1302 can be configured to perform a certain function or operation by executing code, stored on instruction memory 1308, embodying the function or operation. For example, processors 1302 can be configured to perform one or more of any function, step, method, or operation disclosed herein.

Instruction memory 1308 can store instructions that can be accessed (e.g., read) and executed by processors 1302. For example, instruction memory 1308 can be a non-transitory, computer-readable storage medium such as a read-only memory (ROM), an electrically erasable programmable read-only memory (EEPROM), flash memory, a removable disk, CD-ROM, any non-volatile memory, or any other suitable memory.

Processors 1302 can store data to, and read data from, working memory 1304. For example, processors 1302 can store a working set of instructions to working memory 1304, such as instructions loaded from instruction memory 1308. Processors 1302 can also use working memory 1304 to store dynamic data created during the operation of cryoablation computing device 102. Working memory 1304 can be a random access memory (RAM) such as a static random access memory (SRAM) or dynamic random access memory (DRAM), or any other suitable memory.

Input-output devices 1306 can include any suitable device that allows for data input or output. For example, input-output devices 1306 can include one or more of a keyboard, a touchpad, a mouse, a stylus, a touchscreen, a physical button, a speaker, a microphone, or any other suitable input or output device.

Communication port(s) 1314 can include, for example, a serial port such as a universal asynchronous receiver/transmitter (UART) connection, a Universal Serial Bus (USB) connection, or any other suitable communication port or connection. In some examples, communication port(s) 1314 allows for the programming of executable instructions in instruction memory 1308. In some examples, communication port(s) 1314 allow for the transfer (e.g., uploading or downloading) of data, such as ice formation measurement data and the like.

Display 1316 can display a user interface 1318. User interfaces 1318 can enable user interaction with the cryoablation computing device 102. For example, user interface 1318 can be a user interface that allows an operator to interact, communicate, control and/or modify different messages, settings, or features that may be presented or otherwise displayed to a user. The user interface 1318 can include a slider bar, dialogue box, or other input field that allows the user to control, communicate or modify a setting, limitation or input that is used in a cryoablation treatment. In addition, the user interface 1318 can include one or more input fields or controls that allow a user to modify or control optional features or customizable aspects of the cryoablation computing device 102 and/or the operating parameters of the cryoablation system 100. In some examples, a user can interact with user interface 1318 by engaging input-output devices 1306. In some examples, display 1316 can be a touchscreen, where user interface 1318 is displayed on the touchscreen. In other examples, display 1316 can be a computer display that can be interacted with using a mouse or keyboard.

Transceiver 1312 allows for communication with a network. In some examples, transceiver 1312 is selected based on the type of communication network cryoablation computing device 102 will be operating in. Processor(s) 1302 is operable to receive data from, or send data to, a network, such as wired or wireless network that couples the elements of the cryoablation system 100.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cryoablation probe comprising:
   an outer shell comprising a distal end;
   a cryogen supply positioned inside the outer shell, the cryogen supply configured to deliver a cryogen to form ice around the distal end of the outer shell to perform a cryoablation treatment;
   a plurality of heating portions positioned on or in the outer shell, each heating portion of the plurality of heating portions individually controllable to operate in an energized state and a de-energized state;
   wherein the plurality of heating portions comprises:
   a first array of heating portions positioned at a first longitudinal position from the distal end of the cryoablation probe; and
   a second array of heating portions located at a second longitudinal position from the distal end of the cryoablation probe; and
   at least one computing device coupled to the plurality of heating portions, the at least one computing device configured to:
   obtain ice formation data characterizing a size and shape of ice forming at a target tissue in a patient, wherein the ice formation data comprises data characterizing rates of ice growth along different directions from a first predetermined location on the cryoprobe;

compare the ice formation data to a predetermined ice formation profile; and automatically energize a heating portion of the plurality of heating portions based on the comparison of the ice formation data to the predetermined ice formation profile to limit growth of ice in a first direction relative to a second predetermined location on the cryoablation probe while cryogen flows to a tip of the cryoprobe.

2. The cryoablation probe of claim 1, wherein each heating portion of the plurality of heating portions comprises a resistive heating element.

3. The cryoablation probe of claim 1, wherein each heating portion of the plurality of heating portions is coupled to a heater controller that is configured to change one or more heating portions of the plurality of heating portions from the de-energized state to the energized state to change an ice growth characteristic of the ice forming during a freezing cycle of the cryoablation treatment.

4. The cryoablation probe of claim 1, wherein each heating portion of the first array of heating portions is located at a different circumferential position around a center axis of the cryoablation probe.

5. The cryoablation probe of claim 1, wherein each heating portion of the plurality of heating portions is separated from adjacent heating portions.

6. The cryoablation probe of claim 1, wherein the plurality of heating portions are located in the outer shell of the probe.

7. The cryoablation probe of claim 1, wherein the outer shell is positioned radially outward of the cryogen supply.

8. The cryoablation probe of claim 1, wherein the at least one computing device is further configured to:

modify at least one operating parameter of the cryoablation apparatus based on the comparison of the ice formation data to the predetermined ice formation profile, the at least one operating parameter of the cryoablation apparatus comprising one of a pressure, flow rate and temperature of a cryogen.

9. The cryoablation apparatus of claim 1, wherein the first array of heating portions is embedded in the outer shell.

10. The cryoablation apparatus of claim 1, wherein the comparison of the ice formation data to the predetermined ice formation profile comprises comparing ice growth to a desired final size, shape, location, and duration.

* * * * *